United States Patent

Janeiro et al.

[11] Patent Number: 5,892,084
[45] Date of Patent: Apr. 6, 1999

[54] AMINOORGANOFUNCTIONALSILOXANES

[75] Inventors: Benigno A. Janeiro, Medford, N.J.; Mark A. Buese, Gainesville, Fla.

[73] Assignee: PCR, Inc., Gainesville, Fla.

[21] Appl. No.: 17,990

[22] Filed: Feb. 3, 1998

[51] Int. Cl.$^6$ ...................................................... C07F 7/10
[52] U.S. Cl. ................................................................ 556/425
[58] Field of Search ............................................ 556/425

[56] References Cited

U.S. PATENT DOCUMENTS

| | | | |
|---|---|---|---|
| 3,775,452 | 11/1973 | Karstedt | 260/429 R |
| 3,814,730 | 6/1974 | Karstedt | 260/46.5 |
| 4,736,049 | 4/1988 | Suzuki et al. | 556/479 |
| 5,026,890 | 6/1991 | Webb et al. | 556/425 X |
| 5,486,634 | 1/1996 | Hahn et al. | 556/425 |

FOREIGN PATENT DOCUMENTS

| | | |
|---|---|---|
| 0321174 | 6/1989 | European Pat. Off. |
| 2185984 | 8/1987 | United Kingdom |

*Primary Examiner*—Paul F. Shaver
*Attorney, Agent, or Firm*—Hedman, Gibson & Costigan, P.C.

[57] ABSTRACT

The invention provides high purity 3-aminopropylmethylsiloxanes of the general formulae:

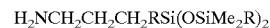

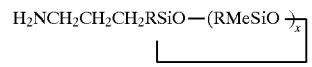

wherein each R may be the same or different aryl group, or monovalent straight or branched chain alkyl group having from 1 to about 18 carbon atoms, Me is methyl, and x may range from about 3 to about 5, the process comprising hydrosilylating allylamine with a monohydridomethylsiloxane of the general formulae:

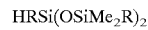

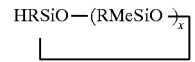

wherein each R may be the same or different aryl group, or monovalent straight or branched chain alkyl group with 1 to about 18 carbon atoms, and x may range from about 3 to about 5, in the presence of a neutral platinum catalyst.

17 Claims, No Drawings

AMINOORGANOFUNCTIONALSILOXANES

FIELD OF THE INVENTION

The present invention relates to high purity 3-aminopropylmethylsiloxanes and a method for their preparation. More specifically, the present invention relates to more than 85% pure 3-aminopropylmethylsiloxane fluids, both linear and cyclic, prepared by hydrosilylation of allylamine by the corresponding hydridomethylsiloxane fluids. These 3-aminopropylmethylsiloxane fluids have utility as intermediates for other derivative organofunctionalsiloxanes, and in cosmetics, textiles, coatings and adhesives.

BACKGROUND OF THE PRESENT INVENTION

There is considerable prior art relating to the synthesis of 3-aminopropylmethylsilanes and siloxanes. U.S. Pat. No. 4,736,049 describes the hydrosilylation of allyl chloride by methyldichlorosilane to produce 3-chloro propylmethyldichlorosilane in 79% yield. In the prior art of producing aminoorganofunctionalsilanes as intermediates for silicones, allyl chloride is hydrosilylated with methyldichlorosilane. Significant amounts of by-products are formed in this reaction, including methyltrichlorosilane, propylmethyldichlorosilane and propene, necessitating distillation to purify the desired product. 3-Chloropropylmethyldichlorosilane may then be alkoxylated, typically with methanol or ethanol, to form the corresponding 3-chloropropyl methyldialkoxysilanes, in high yield, with formation of hydrochloric acid as the by-product. The 3-chloropropylmethyldialkoxysilane may then be converted to the corresponding 3-aminopropylmethyldialkoxysilane by ammonolysis, with requires high pressure equipment since ammonia is used both as a reactant and a solvent. Even with a large excess of ammonia, formation of the secondary amine, bis(dialkoxymethylsilylpropyl) amine occurs to a significant degree, diminishing the yield of the desired primary amine. Filtration of the by-product ammonium chloride is also required in this process.

British Patent No. 2,185,984 describes a synthesis of aminopropylsiloxanes, in approximately a 75% yield, by hydrosilylation of various ketimines, such as N-2 (butylidene)allylamine, with bis(trimethylsiloxy) methylsilane, followed by hydrolysis. The resultant product is a mixture of 71–63% 3-aminopropyl- and 29–37% 2-aminopropyl-substituted siloxanes, indicating that this hydrosilylation process does not produce a single isomeric product. Separation of these isomers, by distillation, is difficult and the overall yield of the 3-(3-aminopropyl) heptamethyltrisiloxane is only slightly better than 50%.

European Patent No. 0 321 174 states that aminopropylsiloxanes can be prepared by hydrosilylation of allylamine with an organohydrogensiloxane in the presence of a base and a rhodium catalyst. Our attempts to duplicate this process failed.

A simple high yielding process for producing 3-aminopropylsiloxanes, substantially free of isomeric 2-aminopropylsiloxanes, has clearly been sought for years to no avail.

SUMMARY OF THE INVENTION

The present invention provides greater than about 85% purity, preferably greater than about 95% purity, of 3-aminopropylmethylsiloxanes of the general formulae:

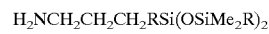

wherein each R may be the same or different aryl group, or monovalent straight or branched chain alkyl group having from 1 to about 18 carbon atoms, Me is methyl, and x may range from about 3 to about 5. The yield of 3-aminopropylmethylsiloxanes from the present invention is greater than about 85%.

The present invention also provides a simple method for rapidly producing 3-aminopropylmethylsiloxanes of the general formulae

wherein each R may be the same or different aryl group, or monovalent straight or branched chain alkyl group having from 1 to about 18 carbon atoms, Me is methyl and x may range from about 3 to about 5, the method comprising hydrosilylating allylamine with the corresponding hydridomethylsiloxanes of the general formulae,

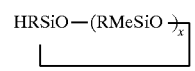

wherein each R may be the same or different aryl group, or monovalent straight or branched chain alkyl group having from 1 to about 18 carbon atoms, and x may range from about 3 to about 5, using a neutral platinum catalyst.

DETAILED DESCRIPTION OF THE PRESENT INVENTION

The present invention provides greater than 85% purity 3-aminopropylmethylsiloxanes of the general formulae:

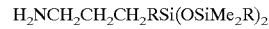

wherein each R may be the same or different aryl group, or monovalent straight or branched chain alkyl group having from 1 to about 18 carbon atoms, Me is methyl and x may range from about 3 to about 5.

The 3-aminoorganofunctionalsiloxanes of the present invention are prepared by hydrosilylating an allylamine with the corresponding monohydridomethylsiloxane of the general formulae

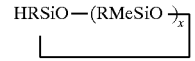

wherein each R may be the same or different aryl group, or monovalent straight or branched chain alkyl group having from 1 to about 18 carbon atoms, Me is methyl, and x may range from about 3 to about 5, in the presence of a neutral platinum catalyst, such as Karsted's.

Monohydridomethylsiloxanes suitable for use in the process of the present invention, and methods for their preparation are well known to those skilled in the art. Specific examples include, but are not limited to, bis(trimethylsiloxy) methylsilane, bis(trimethylsiloxy)phenylsilane, pentamethyldisiloxane, heptamethylcyclotetrasiloxane and nonamethylcyclopentasiloxane.

The preferred unsaturated amine is allylamine.

The hydrosilylation reaction may be carried out at temperatures ranging from about 40° C. to about 150°, preferably between about 65° C. and about 95° C., in the presence of a catalyst.

The catalysts that are known in the art are preferably comprised of platinum or complexes of platinum. They include, but are not limited to, chloroplatinic acid, platinum acetylacetonate, complexes of platinous halides with unsaturated compounds such as ethylene, propylene, organovinylsiloxanes and styrene, hexamethyldiplatinum, $PtCl_2$, $PtCl_3$, $Pt(CN)_3$, and mixtures of any of the foregoing.

The preferred catalyst is platinum complexed with tetravinyltetramethylcyclotetrasiloxane as disclosed in U.S. Pat. Nos. 3,775,452 and 3,814,730.

Sufficient platinum catalyst should be used to provide an effective hydrosilylation reaction. The preferred amount of platinum catalyst used in the process of the present invention ranges from about 5 to about 150 parts by weight of platinum per million parts of combined weights of siloxane and unsaturated amine.

Variations of the present invention will suggest themselves to those skilled in the art in light of the above-detailed description. For example, a mixture of monohydridomethylsiloxanes, of the above-described types, could be used to hydrosilylate allylamine to produce a mixture of 3-aminopropylmethylsiloxanes. All such modifications are within the full intended scope of the appended claims.

DESCRIPTION OF THE PREFERRED EMBODIMENTS

The following examples illustrate the present invention. They are not to be construed to limit the scope of the appended claims in any manner whatsoever.

EXAMPLE 1

A 100 ml flask equipped with magnetic stirring, reflux condenser, pot thermometer, and sampling port was charged with 15 g (0.26 mole) of allylamine and 60 g (0.27 mole) of bis(trimethylsiloxy)methylsilane and was then heated to reflux (69° C.) Once at reflux, 225 µl of 3% Pt complexed with tetravinyltetramethylcyclotetrasiloxane was added. The pot temperature exothermed to 95° C., where it was maintained for 3 hr. The reaction was shown by GC analysis to be complete, resulting in 100% reaction of the allylamine. Excess bis(trimethylsiloxy)methylsilane was distilled off and the product was flash distilled at 80° C. at 10 mm Hg pressure. The product, 3-aminopropyl-bis(trimethylsiloxy) methylsilane, was obtained in 95% distilled yield based on allylamine. The product's identity was confirmed by GC Mass Spectrometry, $^1H$ NMR, and FTIR. The 3-aminoproyl- to 2-aminopropyl- isomer ratio of the products was 19/1.

EXAMPLE 2

In a 250 ml 3-neck RB flask equipped with a magnetic stirring bar, a thermometer well and thermometer, a glass stopper and a reflux condenser, was placed 15.5 g (272 mmoles) of allyl amine and 85.6 g (290 mmoles) of 97% heptamethylcyclotetrasiloxane. The mixture was heated to reflux (80° C.) and 120 µl of platinum 1,3-divinyltetramethyldisiloxane complex (5% Pt) was added. After 70 minutes an exothermic reaction occurred and the temperature increased to 100° C. After 150 minutes a gas chromatographic analysis indicated that all of the allyl amine was consumed and a 7.3:1 ratio of addition products resulted which were assigned after analysis by proton nuclear magnetic resonance as the isomers: 3-aminopropylheptamethylcyclotetrasiloxane and 2-amino-1-methylethylheptamethylcyclotetrasiloxane, respectively. A simple distillation at 91°–92° C. and 3.3 mm Hg yielded 64 g (175 mmoles) of 88% pure 3-aminopropyl heptamethylcyclotetrasiloxane. The distillation pot residue was approximately 30% of the product by gas chromatographic analysis. $^1H$ NMR 400 MHz, $CDCl_3$: δ: 0.05 (M 21H), 0.5 (m 2H), 0.95* (d 0.1H), 1.15 (s 2H), 1.55 (m 2H), 2.65 (m 2H) where all signals are for the major isomer except * for a small amount of the minor isomer; IR (neat liquid on NaCl): $cm^{-1}$: 3420 (vw), 3290 (vw), 2970 (s), 2910 (m), 2850 (w), 1615 (vw), 1565 (vw), 1440 (vw), 1405 (w), 1270 (vs), 1080 (vs), 805 (vs), 750 (vw), 710 (w).

EXAMPLE 3

A 100 ml flask was equipped with a magnetic stirrer, reflux condenser, pot thermometer, and a sampling port. The flask was loaded with 30 g (0.105 mole) of bis (trimethylsiloxy)phenylsilane and 6 g (0.105) mole of allylamine and heated to reflux (79° C.). 180 µl of 3% Pt complexed with tetravinyltetramethylcyclotetrasiloxane were added. The mixture was heated to 125° C. and held for one hour. Thirty one grams (86%) of 3-aminopropyl-bis (trimethylsiloxy)phenylsilane were produced. None of the isomeric 2-aminopropyl-bis(trimethylsiloxy)phenylsilane was formed.

Comparative Example A

A 250 ml flask was equipped with a magnetic stirrer, reflux condenser, pot thermometer, addition funnel, and a sampling port. The flask was loaded with 26 g of xylene, 0.0775 g of $RhCl_3$ trihydrate, and 0.0705 g of NaOH powder and heated to 130° C. The addition funnel was loaded with 31 g of a polymethylhydrosiloxane (0.52 mole SiH) and 36 g (0.63 mole) of allylamine. At a pot temperature of 130° C., the mixture was added at a rate to maintain a constant temperature. As soon as the mixture was added, an immediate evolution of hydrogen was observed. The reaction mixture gelled. No product could be isolated from the gel.

Comparative Example B

A 100 ml flask was equipped with a magnetic stirrer, reflux condenser, pot thermometer, addition funnel and a sampling port. The flask was loaded with 31 g (0.51 mole) of polymethylhydrosiloxane and 36 g (0.63 mole) of allylamine and heated to reflux (62° C.). Once at reflux, 330 µL of 3% Pt complexed with tetravinlytetramethylcyclotetrasiloxane was added.

Evolution of hydrogen was observed throughout the reaction. The reaction mixture eventually gelled and no product could be isolated from the gel.

Comparative Example C

A 100 ml flask was equipped with a magnetic stirrer, reflux condenser, pot thermometer, addition funnel, and a sampling port. The flask was loaded with 13 g (0.22 mole) of tetramethylcyclotetrasiloxane and heated to 100° C. 110 μl of 3% Pt complexed with tetravinyltetramethylcyclotetrasiloxane were added to the pot. The addition funnel was charged with 9.7 g (0.17 mole) of allylamine. The allylamine addition was exothermic and the reaction temperature reached 120° C. The reaction mixture gelled and no product could be isolated from the gel.

All of the above-referenced patents, publications and test methods are hereby incorporated by reference.

Many variations of the present invention will suggest themselves to those skilled in the art in light of the above-detailed description. All such modifications are within the full intended scope of the appended claims.

We claim:

1. A process for the preparation of greater than 85% isomeric purity 3-aminooroganopropylmethylsiloxanes, said process comprising hydrosilylating an allylamine with a monohydridomethylsiloxane in the presence of a neutral platinum catalyst.

2. A process as defined in claim 1 wherein said monohydridmethylsiloxane is selected from those of the general formulae:

HRSi(OSiMe$_2$R)$_2$

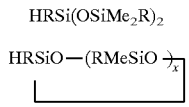

wherein each R may be the same or different aryl group, or monovalent straight or branched chain alkyl group with 1 to about 18 carbon atoms, Me is methyl and x may range from about 3 to about 5.

3. A process for the preparation of greater than 85% isomeric purity 3-aminopropylmethylsiloxanes of the general formula:

H$_2$NCH$_2$CH$_2$CH$_2$RSi(OSiMe$_2$R)$_2$

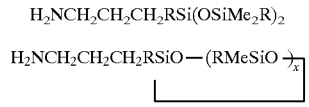

wherein each R may be the same or different aryl group, or monovalent straight or branched chain alkyl group having from 1 to about 18 carbon atoms, Me is methyl, and x may range from about 3 to about 5, said process comprising hydrosilylating allylamine with a monohydridomethylsiloxane of the general formulae:

HRSi(OSiMe$_2$R)$_2$

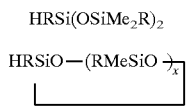

wherein R, Me an x are as defined above, in the presence of a neutral platinum catalyst.

4. A process according to claim 3 wherein the monohyridomethylsiloxane is selected from the group consisting of bis(trimethylsiloxy)methylsilane, heptamethylcyclotetrasiloxane, nonamethylcyclopentasiloxane, and mixtures of any of the foregoing.

5. A process according to claim 3 wherein said platinum catalyst is a complex of platinous chloride and divinyltetramethyldisiloxane.

6. A process according to claim 3 wherein said platinum catalyst is a complex of platinous chloride and 1,3,5,7-tetravinyltetramethylcyclotetrasiloxane.

7. A process according to claim 3 wherein the platinum catalyst is present in an amount ranging from about 5 to about 150 parts by weight of platinum per million parts of combined weights of monohydridomethylsiloxane and allylamine.

8. A process according to claim 3 wherein said hydrosilylation reaction is carried out at a temperature ranging from about 40° C. to about 150° C.

9. A process according to claim 8 wherein said hydrosilylation reaction is carried out at a temperature ranging from about 65° C. to about 95° C.

10. A composition comprising greater than 85% isomeric purity 3-aminoorganofunctionalsiloxane produced by the process according to claim 1.

11. A composition as defined in claim 10 having greater than 85% isomeric purity 3-aminopropylmethylsiloxane.

12. A composition comprising greater than 85% isomeric purity 3-aminopropylmethylsiloxane of the general formula H$_2$NCH$_2$CH$_2$CH$_2$RSi(OSiMe$_2$R)$_2$

wherein each R may be the same or different aryl group, or monovalent straight or branched chain alkyl group having from 1 to about 18 carbon atoms, Me is methyl, and x may range from about 3 to about 5, and produced by the process according to claim 3.

13. A composition according to claim 12 wherein each R is methyl.

14. A high purity 3-(3-aminopropyl)heptamethyltri- siloxane according to claim 13 having an isomeric purity greater than 95%.

15. A composition according to claim 12 wherein each R is methyl and x ranges from 3 to 4.

16. A high purity 3-aminopropylheptamethylcyclotetrasiloxane according to claim 15 wherein x is 3 and having an isomeric purity greater than 85%.

17. A high purity 3-aminopropylnonamethylcyclopentasiloxane according to claim 15 wherein x is 4 and having an isomeric purity greater than 85%.

* * * * *